United States Patent
Behan et al.

(12)

(10) Patent No.: US 6,241,979 B1
(45) Date of Patent: Jun. 5, 2001

(54) PERFUMED PRODUCTS CONTAINING A MIXTURE OF PERFUME MATERIALS HAVING ANTIBACTERIAL PROPERTIES

(75) Inventors: John Martin Behan, Ashford; Tony Minhas, Dartford; Alan Forbes Provan; David Charles Hooper, both of Ashford, all of (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/284,192

(22) PCT Filed: Oct. 8, 1997

(86) PCT No.: PCT/GB97/02770

§ 371 Date: Jun. 7, 1999

§ 102(e) Date: Jun. 7, 1999

(87) PCT Pub. No.: WO98/16194

PCT Pub. Date: Apr. 23, 1998

(30) Foreign Application Priority Data

Oct. 11, 1996 (EP) .................................................. 96307436

(51) Int. Cl.[7] .............................. A61L 9/00; A01N 65/00; A61K 7/50; A61K 7/46
(52) U.S. Cl. .................... 424/76.1; 424/195.1; 510/130; 512/1
(58) Field of Search ............................... 424/195.1, 76.1; 510/130; 512/1

(56) References Cited

U.S. PATENT DOCUMENTS

| | | | |
|---|---|---|---|
| 5,354,737 | * 10/1994 | Barr et al. | 512/17 |
| 5,420,104 | * 5/1995 | Holzner et al. | 512/2 |
| 5,540,853 | * 7/1996 | Trinh et al. | 510/101 |
| 5,756,145 | * 5/1998 | Darouiche | 427/2.24 |
| 5,833,999 | * 11/1998 | Trinh et al. | 424/401 |
| 5,853,745 | * 12/1998 | Darouiche | 424/423 |

FOREIGN PATENT DOCUMENTS 451 889   10/1991   (EP) .
2 540 382   8/1984   (FR) .

OTHER PUBLICATIONS

Database WPI Week 9602 Derwent Publications Ltd., London, GB; AN 96–017528 XP 002027041 & JP 07 292 390 A (Raku KK), Nov. 7, 1995.
Database WPI Week 9432 Derwent Publications Ltd., London, GB; AN 94–255839 XP002027042 & CA 2 111 523 A (Eastman Kodak), Jun. 17, 1994.
Database WPI Week 9430 Derwent Publications Ltd, London, GB, AN 94–245645 XP002027043 & JP 06 179 610 A (Shiseido Co. Ltd., et al) Jun. 28, 1994.
Database WPI Week 9409 Derwent Publications Ltd., London,GB; AN 94–071823 XP002027044 & JP 06 024 952 A (Inahata Koruo KK), Feb. 1, 1994.
Database WPI Week 8722 Derwent Publications Ltd., London, GB, AN 87–153294 XP002027045 & JP 62–089 800 A (Lion Corp.), Apr. 24, 1987.
Database WPI Week 9644 Derwent Publications Ltd. London, GB; AN 96–441492 XP002027046 & RU 2 053 258 C ( Partner Stock Co), Jan. 27, 1996.
Database WPI Week 9346 Derwent Publications Ltd., London, GB; AN 93–365135 XP002027047 & JP 05 271 064 A (Dainippon Jochugiku KK) Oct. 19, 1993.
Patent Abstract of Japan vol. 15, No. 445 (C–884), Nov. 13, 1991 & JP 03 190815 A ( Kobayashi Kose Co Ltd.), Aug. 20, 1991.
Database WPI Week 8949 Derwent Publications Ltd., London, GB; AN 89–356879 XP002027048 & CN 1 030 184 A (Fact. Trad. Ch. Med.), Jan. 11, 1989.

* cited by examiner

*Primary Examiner*—David M. Naff
*Assistant Examiner*—Mike Meller
(74) *Attorney, Agent, or Firm*—Pillsbury Madison & Sutro LLP

(57) ABSTRACT

A perfumed product containing an antibacterial agent and a perfume material is prepared. The perfumed product can contain triclosan as the antibacterial agent and a mixture of perfume materials such as Amberlyn Super PM 577, clover leaf, dihydro myrcenol, phenyl propyl alcohol and terpineol alpha.

7 Claims, No Drawings

PERFUMED PRODUCTS CONTAINING A MIXTURE OF PERFUME MATERIALS HAVING ANTIBACTERIAL PROPERTIES

This application is the national phase of international application PCT/GB97/02770 filed Oct. 8, 1997 which designated the U.S.

FIELD OF THE INVENTION

This invention relates to perfumed products.

BACKGROUND OF THE INVENTION

It is common practice to incorporate perfume materials in various products, such as personal, domestic and industrial cleaning and hygiene products, for aesthetic reasons. It is also known that certain perfume materials have antimicrobial properties, that is, as well as having pleasant odour characteristics these materials are also effective to kill or inhibit at least certain microorganisms such as bacteria, fungi, yeasts, viruses.

EP 0451889 discloses a number of antimicrobially effective perfume material, including phenylethyl formate, trans-2-hexenal, cis-3-hexenyl acetate, phenylacetaldehyde, cinnamic aldehyde, phenylacetic acid, cinnamic acid, benzyl formate, prenyl acetate, 2-methyl-2-hepten-6-one, methyl hexyl ketone, methyl amyl ketone, amyl propionate, amyl acetate and methyl benzoate, and describes their use in a range of products including shampoo, skin lotion, dishwashing liquid etc.

U.S. Pat. No. 5,420,104 concerns perfuming compositions having antimicrobial and deodorant properties, and their use in products such as soap, detergent and fabric softener.

The present invention is based on the discovery of various additional materials having both perfuming and antibacterial properties.

SUMMARY OF THE INVENTION

In one aspect, the present invention provides a perfumed product comprising at least one perfume material having antibacterial properties and selected from the group comprising: Amberlyn Super PM 577, clove leaf, dihydro myrcenol, phenyl propyl alcohol and terpineol alpha.

Amberlyn Super PM 577 is the trade name of a material containing as its active ingredient Amberlyn, which has the chemical name, dodecahydro-3a,6,6,9a-tetramethylnaphtho[2,1-b]furan available from Quest International.

The invention also covers use of at least one of Amberlyn Super PM 577, clove leaf, dihydro myrcenol, phenyl propyl alcohol or terpineol alpha as an antibacterial agent in a perfumed product.

The term "perfume material" is used to mean a material that imparts to the product fragrance or odour characteristics that are generally considered at least inoffensive and preferably pleasing to intended users of the product.

The term "antibacterial properties" is used to mean effective to kill, inhibit or inactivate at least a proportion of one or more strains of bacteria.

The product is typically a personal, domestic or industrial cleaning of hygiene product. Examples of products to which the invention is applicable include soaps (in bar and liquid form), non-soap detergent bars, non-soap liquid cleaners, deodorants, anti-perspirants, hair care products such as shampoos and conditioners, bath and shower gels and foam products, oral hygiene products such as toothpastes, mouth washes and dental floss, shaving foams, skin lotions and creams, laundry products such as fabric washing powders and liquids, fabric conditioners and fabric softeners, hard surface cleaning products, pet cleaning shampoos and powders, carpet cleaners etc.

The product may comprise more than one of the specified perfume materials. The product may also comprise one or more additional perfume materials, which may or may not have antibacterial properties. For example, good results have been obtained with three mixtures of perfume ingredients, referred to as perfumes 1, 2 and 3, containing the following materials in the specified amounts (by weight):

|  | 1 | 2 | 3 |
|---|---|---|---|
| Amberlyn Super PM 577 | 0.50 | 0.40 | 0.50 |
| Citronellol standard | — | 2.70 | 2.70 |
| Clove leaf | 4.50 | 3.20 | 3.60 |
| Dihydro myrcenol | 5.50 | 3.50 | 3.50 |
| Styrally acetate | 3.00 | 2.00 | 2.00 |
| Benzyl alcohol | 10.00 | — | 10.40 |
| Ethyl vanillin | 0.10 | 0.10 | 0.10 |
| Moss oakmoss | — | 0.40 | 0.40 |
| Phenyl propyl alcohol | 2.70 | 2.00 | 2.00 |
| Terpineol alpha | 9.00 | 6.00 | 6.00 |
| Tetrahydro linalol | — | 3.00 | 3.00 |

Preferred combinations are Amberlyn Super PM 577 and/or citronellol standard and/or clove leaf and/or dihydro myrcenol and/or styrallyl acetate. Such combinations optionally also include benzyl alcohol and/or ethyl vanillin and/or moss oakmoss and/or phenyl propyl alcohol and/or terpineol alpha and/or tetrahydro linalol.

When incorporated in a toilet soap bar each of perfumes 1, 2 and 3 have been found to give good antibacterial properties.

The antibacterial perfume materials of the invention may be used to replace, in whole or in part, conventional antibacterial materials conventionally used in the perfumed products of interest, without diminishing the antibacterial properties of the product. For example, antibacterial soap bars conventionally include antibacterial agents such as triclosan (2', 4, 4'-trichloro-2-hydroxy-diphenyl ether), which is commercially available e.g. under the Trade Mark Irgasan DP 300, and trichlorocarbanalide (TCC) (also known as triclocarban). Triclosan is a broad spectrum antimicrobial agent which is known to provide excellent bacteriostatic activity at low concentrations against both Gram positive bacteria and Gram negative bacteria. Triclosan is the antibacterial commonly used in antibacterial soaps. TCC is effective only against Gram positive bacteria. TCC may be used in some antibacterial soaps, usually in combination with triclosan. By incorporating one or more antibacterial perfume materials of the invention into such products, the levels of triclosan and/or TCC may be reduced, with consequent cost savings, without reducing the antibacterial efficacy of the product.

In a further aspect, the invention thus provides a perfumed product comprising an antibacterial agent, and at least one perfume material having antibacterial properties and selected from the group comprising Amberlyn Super PM 577, clover leaf, dihydro myrcenol, phenyl propyl alcohol and terpineol alpha.

The antibacterial agent may comprise one or more of the many materials conventionally used for this purpose, including triclosan, 2,2'-methylene bis (3,4,6-trichlorophenol), 2,4, 4'-trichlorocarbanilide, 3,4,4'-trichlorocarbanilide, 2,5,4'-tribromosalicylanilide, 3-trifluoromethyl-4,4'-dichlorocarbanilide, hexachlorophene, dichlorophenol, trichlorosalycilanilide, tribromosalycilanilide (TBS), and tetrachlorosalycilanilide (TCSA).

Other possible antibacterial agents are listed in McCutcheon's Functional Materials (1994 International Edition and 1994 North American Edition).

The antibacterial agent is conveniently present in an amount in the range 0.01 to 10% by weight, typically 0.25 to 0.75% by weight.

The perfume material is conveniently present in an amount in the range 0.01 to 90% by weight, generally in an amount in the range 0.1% to 60% by weight.

The perfumed product may include additional and optional ingredients appropriate to the product in question, as is known to those skilled in the art.

In products containing an antibacterial agent as well as the perfume material it is thought that a synergistic effect may occur between the two ingredients, with the two ingredients in combination giving a greater combined antibacterial effect than would be expected by simply adding together the antibacterial effect of each component.

The invention will be further described, by way of illustration, in the following examples.

The examples concern experiments with antibacterial soap bars to measure antibacterial efficacy using three different tests:

1. Bacterial contact time test (BCT)—Example 1
2. Finger imprint test—Example 2
3. Agar patch test—Example 3

The experiments were carried out with reference to a soap bar having the composition of a commercially available antibacterial soap bar comprising a palm blend/but oil base with conventional antibacterial agents in the form of 0.23% triclosan and 0.02% TCC, with 1.3% of a perfume known as TS 118L. (TS 118L does not include any of the perfume materials of the invention.)

Comparable experiments were carried out on soap bars in accordance with the invention that were generally similar to the reference bar but included a perfume known as BioPink (having the composition of perfume 1 as given above) in place of TS 118L, with either similar or reduced levels of triclosan.

In the examples, all % are % by weight unless otherwise stated.

All of the examples used a conventional soap base in the form of a 75/25 palm blend/nut oil formulation, referred to as rCN base because the nut oil is refined coconut (CN) oil. The soap base was made into soap bars in conventional manner. In some cases, the bars incorporated the known anti-bacterial agents triclosan (at the current conventional level of 0.23% and at the reduced level of 0.18%) and also TCC (at a level of 0.02%). Some bars also incorporated one of two perfumes, known as TS 118L (prior art) and BioPink (in accordance with the invention).

Triclosan and TCC were dosed into the soap base as a mixture in perfume. The soap base was milled three times to ensure proper dispersion, and the levels of antibacterials quantified by extraction and gas chromatography. Previous studies have shown this method of incorporating antibacterials and perfume gives homogenous distributions in the soap bars. All bars that contained triclosan also contained 0.02% TCC.

The bars tested were:
rCN base only
rCN base+0.18% triclosan+0.02% TCC
rCN base+0.23% triclosan+0.02% TCC
rCN base+0.18% triclosan+0.02% TCC+perfume (TS 118L at 1.3%)
rCN base+0.23% triclosan+0.02% TCC+perfume (TS 118L at 1.3%)
rCN base+0.18% triclosan+0.02% TCC+BioPink perfume at 1.3%
rCN base+0.23% triclosan+0.02% TCC+BioPink perfume at 1.3%

As noted above, the bar comprising rCN base+0.23% triclosan+0.02% TCC+TS 118L at 1.3% has the composition of a commercially available antibacterial soap bar, and so represents prior art with which bars including the BioPink perfume can be compared.

EXAMPLE 1

Bacterial Contact Time Test

The in vitro bacterial contact time (BCT) test provides a measure of the efficacy with which a product solution, at a typical concentration representing wash water, will kill a given type of bacteria introduced into that soap solution. Bacterial kill is measured by sampling the bacteria/wash water mixture at short time intervals after mixing, stopping the kill action, and then growing the remaining viable bacteria into colonies which can be counted. The measure of bacterial kill is in the form of the time taken to achieve a given level of bacterial kill, usually 99.9%.

The BCT test provides a measure of the efficacy of effects from both the product base (soap) and any component which may have antibacterial action. Further, the BCT test gives a measure of effects in solution and not on skin.

Bacteria are classified in terms of their response to a staining process used in the laboratory to help make these microorganisms more clearly visible under the microscope. This stain is called Gram's stain and bacteria that appear under the microscope stained blue/purple are classified as Gram positive and those that stain red/pink are classified as Gram negative.

A well known Gram positive bacterial species that forms part of the normal skin flora is *Staphylococcus aureus*. This species is classified as an opportunistic pathogen. If the skin surface becomes damaged it is vulnerable to infection by *S. aureus*, resulting in the formation of pimples, spots, boils and other skin infections.

*Escherichia coli* (*E. coli*) is a Gram negative bacterial species that is primarily a gut pathogen causing intestinal upsets such as diarrhoea. However, *E. coli* is considered a transient pathogen on skin, since it can be easily transferred from the hands to the mouth and cause infections.

*Klebsiella pneumoniae* is a Gram negative species that is considered an a gut pathogen an is associated with intestinal upsets and sometimes respiratory infections. This species is not part of the main skin microbial flora but can cause infection if transferred from hands to the mouth.

The BCT test was employed to demonstrate bactericidal activity as a function of the time required to kill greater than 99.9% of *Staphylococcus aureus, Escherichia coli* and *Klebsiella pneumoniae* microorganisms. This test was developed in the late 1960's to evaluate the bactericidal activity of various household and personal products.

Two consecutive 10 ml broth transfers of each bacterial species were made into Tryptone Soya Broth (Oxoid). All broths were incubated for 24 hours at 35° C. Second day cultures were used in this assay (approximately $10^8$ cells/ml). The broth cultures of each species were estimated (total viable counts) and found to be approximately $10^8$ cells/ml.

For the tests, soap bars were dispersed into sterile deionised water as 8% w/v slurries, the estimated in-use concentration of soap bars.

The BCT test was performed by pipetting 1 ml of each soap solution into 30 ml sterile universal tubes. One ml of the culture inoculum, containing approximately $2 \times 10^6$ cells/ml, was added to each test solution. The mixtures were sampled at 15 second intervals for the first minute, and then every minute up to 5 minutes. Calibrated 10 µl loops were used for withdrawing samples at the predetermined intervals. Each loop sample was immediately placed into 8 ml of sterile molten (45° C.) MCTA (Microbial Content Test Agar, Difco) in flat-sided bottles and gently mixed. The MCTA medium was used to ensure that the actives and perfume were effectively neutralised antibacterial activity. Bottles were laid to allow the agar to solidify before being incubated at 35° C. for 24 hours to allow colony development. After incubation, the colonies were enumerated.

Each $10^6$ cfu/ml culture preparation was diluted a thousand-fold by preparing three 1:10 serial dilutions in 9 ml peptone water. In a control bottle, 1 ml of this dilution was added to 1 ml of sterile 0.1% peptone water (instead of soap solution). Eight replicate samples were withdrawn with a 10 µl loop and mixed with the molten agar and incubated as above. The average colony count obtained represented the 99.9% endpoint in the test mixtures; the results are reported as the time required to obtain a 99.9% kill bacteria.

Results

The BCT test was employed to demonstrate rapid bactericidal activity as a function of the time required to effect a kill of 99.9%. Three bacterial species were used were: *Staphylococcus aureus* ATCC#8739—Gram negative, *Escherichia coli* ATCC#8739—Gram negative, and *Klebsiella pneumoniae* ATCC#10031—Gram negative.

Efficacy Against the Gram Positive *S. aureus*
(Table 1)

*S. aureus* can be a species vulnerable to the effects of alkaline detergents and antibacterials. As a results the data in Table 1 show that the rCN base alone is effective at reducing the number of *S. aureus* (99.9% kill) within 30 seconds.

When the antibacterial agents triclosan (0.18%) and TCC (0.02%) are present, the rate of kill is more rapid (within 15 seconds). The effect of increasing triclosan levels (0.23%) or the addition of perfume to the soap bar could not be measured since the rate of kill was so rapid. The minimum time possible to sample and quench the solution/bacteria system is 15 seconds. It is probable that the higher level of antibacterial effected the 99.9% kill more rapidly that the lower level.

TABLE 1

*S. aureus* - Bactericidal Contact Time Test

| Product Description | Time for 99.9% kill |
| --- | --- |
| Unperfumed | |
| rCN Base only | 30 seconds |
| rCN Base + 0.18% triclosan + 0.02% TCC | 15 seconds |
| rCN Base + 0.23% triclosan + 0.02% TCC | 15 seconds |

TABLE 1-continued

*S. aureus* - Bactericidal Contact Time Test

| Product Description | Time for 99.9% kill |
| --- | --- |
| With TS 118L perfume | |
| rCN Base + 0.18% triclosan + 0.02% TCC | 15 seconds |
| rCN Base + 0.23% triclosan + 0.02% TCC | 15 seconds |
| With BioPink perfume | |
| rCN Base + 0.18% triclosan + 0.02% TCC | 15 seconds |
| rCN Base + 0.23% triclosan + 0.02% TCC | 15 seconds |

It can only be concluded, from this data, that soap containing antibacterial (triclosan) will kill *S. aureus* bacteria more effectively than will the soap base alone. The vulnerability of the species is such that no advantage for a higher level of antibacterial can be shown. For the same reason it cannot be shown that the BioPink perfume offers any advantage.

Efficacy Against Gram Negative *E. coli* (Table 2)

Effective action against the bacterial type *E. coli* is important because through transfer from fingers to mouth, perhaps via handling of foodstuffs, such bacteria can gain access to the intestines where they can induce diarrhoea and other intestinal upsets.

*E. coli* bacteria are more difficult to kill than *S. aureus*. The data in Table 2 show the time for 99.9% kill of *E. coli* by the rCN base alone as 120 seconds, compared to 30 seconds for *S. aureus*. However, the advantage of the longer time is that is now possible to discriminate between effects from different levels of antibacterial and from the perfume.

The presence of triclosan in the soap base at 0.18% reduced the kill time to within 60 seconds. The soap bar containing 0.23% triclosan showed an even faster rate of kill of 45 seconds.

Soap bars containing triclosan and perfume (TS 118L) demonstrated that the perfume may add to the anti-bacterial activity of triclosan, since the rate of kill by the TS 118L perfume+0.18% triclosan was faster (45 seconds) than the unperfumed bar containing 0.18% triclosan (60 seconds). Furthermore, the bar perfumed with TS 118L+0.23% triclosan showed an even faster kill time of 30 seconds.

These data demonstrate that the BCT test shows good sensitivity when it is used with an appropriate and important bacteria type.

TABLE 2

*E. coli* - Bactericidal Contact Time Test.

| Product Description | Time for 99.9% kill |
| --- | --- |
| Unperfumed | |
| rCN Base only | 120 seconds |
| rCN Base + 0.18% triclosan + 0.02% TCC | 60 seconds |
| rCN Base + 0.23% triclosan + 0.02% TCC | 45 seconds |
| With TS 118L perfume | |
| rCN Base + 0.18% triclosan + 0.02% TCC | 45 seconds |
| rCN Base + 0.23% triclosan + 0.02% TCC | 30 seconds |

TABLE 2-continued

E. coli - Bactericidal Contact Time Test.

| Product Description | Time for 99.9% kill |
| --- | --- |
| With BioPink perfume | |
| rCN Base + 0.18% triclosan + 0.02% TCC | 30 seconds |
| rCN Base + 0.23% triclosan + 0.02% TCC | 15 seconds |

Most importantly, the bars perfumed with BioPink showed the most effective kill times.

The soap perfumed with BioPink and a lower level of triclosan (0.18%) matched the performance of the conventional bar containing the higher level of triclosan (0.23%) and TS 118L perfume.

The soap perfumed with BioPink and the higher level of triclosan (0.23%) showed the fastest kill time of 15 seconds.

In brief, the performance in the *E. coli* BCT test of the bar containing TS 118L and 0.23% triclosan was matched by BioPink perfume and reduced levels of triclosan (0.18%).

Efficacy Against Gram Negative *K. pneumoniae* (Table 3)

*Klebsiella pneumoniae,* like *E. coli,* is considered to be a transient pathogen on skin and can cause ill-health if ingested.

Table 3 shows the BCT data for *K. pneumoniae.* This species required the longest time to be killed (99.9%) by the rCN base alone (180 seconds). Addition of triclosan at 0.18% reduced the kill time to 120 seconds. The kill time was further reduced to 60 seconds with soap bars containing either level of triclosan (0.18% & 0.23%) and perfumed with TS 118L. The soap bars perfumed with BioPink perfume and 0.18% triclosan matched the kill time of the conventional bar with 0.23% triclosan and TS 118L perfume. The soap bar containing 0.23% triclosan and BioPink perfume showed an even shorter kill time of 45 seconds.

TABLE 3

*K. pneumoniae* - Bactericidal Contact Time Test

| Product Description | Time for 99.9% kill |
| --- | --- |
| Unperfumed | |
| rCN Base only | 180 seconds |
| rCN Base + 0.18% triclosan + 0.02% TCC | 120 seconds |
| rCN Base + 0.23% triclosan + 0.02% TCC | 120 seconds |
| With TS 118L perfume | |
| rCN Base + 0.18% triclosan + 0.02% TCC | 60 seconds |
| rCN Base + 0.23% triclosan + 0.02% TCC | 60 seconds |
| With BioPink perfume | |
| rCN Base + 0.18% triclosan + 0.02% TCC | 60 seconds |
| rCN Base + 0.23% triclosan + 0.02% TCC | 45 seconds |

Conclusions

The BCT data for all three bacterial species (*S. aureus, E. coli* & *K. pneumoniae*) demonstrated that the presence of triclosan in soap bars (0.18% & 23%) reduced the kill time (99.9% kill) compared with the soap base alone.

The *E. coli* & *K. pneumoniae* data showed that the BCT test clearly demonstrated an ability to discriminate between the efficacies of two levels of triclosan (0.18% & 0.23%) with the higher level of triclosan requiring less time for bacterial kill, and the same was true for the two perfumes (TS 118L & BioPink).

For all three bacterial types, soap containing the BioPink perfume and a lower level of triclosan (0.18%) gave more rapid bacterial kill than the soap base alone.

For all three bacterial types, soap containing the BioPink perfume and a lower level of triclosan (0.18%) effectively matched the performance of the conventional perfumed soap bar containing TS 118L and 0.23% triclosan.

EXAMPLE 2

Finger Imprint Test

The in situ finger imprint test is an indirect measure of the presence of antibacterial agents which have been deposited on human skin. The basis of the test is that skin on which antibacterial may have deposited is placed in contact with the surface of an agar gel containing a standardised quantity of selected bacteria. When the agar plate is then kept under conditions which will allow the bacteria to grow, an area of inhibited growth can be present where the antibacterial has transferred from the skin to the agar gel. If sufficient antibacterial has been transferred, the imprinted area of inhibition may extend beyond the immediate area of contact between the skin and agar, assuming the antibacterial is either water soluble or may be carried in water.

When skin has been washed with a detergent product containing the antibacterial agent and then rinsed/dried, a positive test result indicates deposition, substantivity against rinsing, and a subsequent ability to inhibit the growth of selected bacteria with which the skin is contacted. The level of clearing within the imprint on the agar gel is a measure of the effectiveness of the antibacterial action (using the Vinson scoring system).

In this study the deposition of antibacterial agents on fingers of volunteers was determined immediately after a standardised single wash with the test soap bars, followed by rinsing and drying.

The bottom layer of agar plates were prepared using 10 ml Tryptone Soya Agar (TSA, Oxoid) and then allowed to solidify. An overnight broth culture (Tryptone Soya Broth, Oxoid) of *Staphylococcus aureus* ATCC #6538 or *Klebsiella pneumoniae* ATCC #10031 was diluted 1:100 (using sterile 0.9% NaCl) of which 0.7 ml was added to molten TSA (100 ml—in a water bath at 47° C.) and mixed avoiding air bubbles. Eight milliliters of the molten seeded agar was poured over the bottom layer and allowed to solidify.

Wash Procedure

Subjects were requested to refrain from using any germicidal soap for a minimum of 24 hours before the test. The subjects were asked to rinse their hands under warm running tap water for 15 seconds. They were then given a different soap for each hand and asked to lather for 15 seconds after which the soaps were placed aside and they continued lathering for a further 45 seconds. The hands were rinsed under tap water, avoiding cross-contamination and dried by the study investigator using a small domestic hair dryer.

Without touching anything else, subjects placed their index fingers onto agar plates seeded with S. aureus and their middle fingers onto plates seeded with K. pneumoniae for 30 seconds. The subjects' fingers were then rinsed with ethanol and washed with antibacterial soap. The plates were incubated for 24 hours at 35° C.

Assessment

The plates were assessed by estimating the clarity of the finger imprint area using the Vinson method. (Vinson, L J, Ambye, E L, Bennett, A G, Schneider, W C & Travers, J J 1961. In vivo tests for measuring antibacterial activity of toilet soap and detergent bars. J Pharm Sci 50: 827–830.)

| Score | Level of clearing | Activity |
| --- | --- | --- |
| 0 | No effect on growth of organism | None |
| 1 | Slight patchiness within imprint | Slight |
| 2 | Area showing some inhibition of growth | Moderate |
| 3 | Clearly delineated zone but a little growth present | Strong |
| 4 | Clearly delineated growth-free imprint | Complete Inhibition |

The Vinson scale is such that differences of less than 1 unit cannot be considered meaningful unless supported by data from sufficient panellists to allow a proper statistical interpretation.

Statistical Analysis

The scores of the finger imprints were analysed using the Wilcoxon signed-rank test. Previous studies had shown that the gender, which finger and size of imprint were not statistically significant to affect the level of clearing of imprint area, i.e., the soap bar was the most important determinant of the zone clearing and hence the score.

The difference in level of clearing of the imprint to the soaps used were determined and ranked in order of magnitude, irrespective of the sign (i.e. given a rank order). Panellists showing no differences in scores between the two soaps were excluded from the analysis. The sign of the ranking was then taken into consideration. The rank order scores were totalled as two groups (− or +) and the lowest score was compared with statistical tables to check for significance.

Results

Set A

| Base + 0.18% triclosan + TS 118L | vs | Base + 0.23% triclosan + TS 118L |
| --- | --- | --- |
| When tested against S. aureus: | | 95% significant difference |
| When tested against K. pneumoniae: | | 95% significant difference |

The data for S. aureus and K. pneumoniae demonstrates that the finger imprint test is sensitive enough to discriminate between the effects of the two levels of triclosan after a single was procedure.

Set B

| Base + 0.23% triclosan + TS 118L | vs | Base + 0.18% triclosan + BioPink |
| --- | --- | --- |
| When tested against S. aureus: | | no significant difference (at 90% level) |
| When tested against K. pneumoniae: | | no significant difference (at 90% level) |

The data shows that there was no significant difference between the TS 118L soap bar containing triclosan at 0.23% and the BioPink bar with a reduced level of triclosan (0.18%) i.e. no difference in antibacterial efficacy as measured by the finger imprint test against Gram positive and negative bacterial species.

Set C

| Base + 0.18% triclosan + TS 118L | vs | Base + 0.18% triclosan + BioPink |
| --- | --- | --- |
| When tested against S. aureus: | | significant at 95% |
| When tested against K. pneumoniae: | | significant at 95% |

These soap bars were compared to determine whether the antibacterial performance of the soap bar perfumed with BioPink was superior to TS 118L. The results for S. aureus and K. pneumoniae demonstrate that the soap bar perfumed with BioPink produced statistically significant better scores in the finger imprint test than the bar perfumed with TS 118L.

Conclusions

The finger imprint test, in this study, has been shown (set A) to be sensitive enough to discriminate antibacterial activity between soap bars containing two levels of triclosan (0.18% and 0.23%). This test has also shown (set B) that statistically there is no significant difference between the conventional soap bar containing TS 118L+0.23% triclosan+0.02% TCC and the soap bar perfumed with BioPink and a reduced level of active (0.18% triclosan+ 0.02% TCC). This was demonstrated against S. aureus (Gram positive bacterial species resident on skin) and K. pneumoniae (Gram negative bacterial species, a transient pathogen found on skin).

The final finger imprint test (set C) was clear evidence that the BioPink perfume is more active than the TS 118L, since all other variables were the same. The statistical analysis for S. aureus and K. pneumoniae was in favour of the soap bar perfumed with BioPink.

This example shows that:

Perfume can deliver antibacterial effects

A reduced level of triclosan in conjunction with BioPink perfume can achieve the efficacy corresponding to soap containing a higher level of triclosan (0.23%) with the perfume TS 118L.

EXAMPLE 3

Agar Patch Test

The agar patch test is an in situ test which gives a measure of the effectiveness of antibacterial material which may be deposited on skin from a detergent product during washing. The test can determine effectiveness immediately after washing or some hours later; six hours later in the work described.

The agar patch test does not give a direct measure of bacterial inhibition on skin. The action of washing will itself have reduced the numbers of skin bacteria to a very low level such that they cannot be properly sampled and counted. The principle of the agar patch test is that skin on which a material with antibacterial properties may have deposited during a washing regime is placed in contact with an agar gel containing known numbers of a specific bacteria. If a material with antibacterial properties has deposited on skin, and if that material is capable of transferring from skin to agar, then the subsequent growth of bacteria in the gel will be inhibited. The extent of bacterial growth inhibition is judged by statistical comparison of the numbers of colonies developing for each test product with reference to a control.

To give a positive result in the test, a material with antibacterial properties must deposit from the wash product, must remain active on skin for a period of time, must then transfer to agar gel during contact with the skin and finally must still inhibit bacterial growth.

In the tests reported the skin of each panellist was washed only once with the test or control product concerned and an assay of antibacterial efficacy was made 6 hours after washing.

Each product was tested by 20 panellists (on average) with the objective of determining the residual antibacterial activity 6 hours after a single wash with a soap bar product. Products were assigned in a balanced randomised design. Each subject served as a block for pairwise comparison of products. Effectiveness was measured by the inhibition of S. aureus ATCC #6538 and E. coli NCTC 10418 which were pre-seeded onto the surfaces of agar-filled 35×10 mm petri dishes.

Two consecutive broth transfers of a S. aureus or E. coli cultures were made using Tryptone Soya Broth (Oxoid). The cultures were incubated for 24 hours at 35° C. Second day culture broths were used in this assay (approximately $10^8$ cfu/ml).

The test medium used was Tryptone Soya Agar (TSA-Oxoid). On the day before the test, the petri dish bottoms were filled completely with TSA to form a convex surface and were allowed to solidify and then placed at 30° C. overnight to remove excess moisture. Within 30 minutes of the test, the petri dishes were surface inoculated with approximately 200 cfu.

Subjects were required to wash exclusively with non-germicidal soap for one week prior to the test date. Only a single wash with antibacterial product was given in the test. The order of washing, left arm first or right arm first, was randomised over the panel.

Starting with a wash on the right arm, the left hand was gloved while the right arm was washed. The arm washing procedure involved the subject rinsing the volar surface of the right forearm with warm running tap water for 15 seconds. The subject was then given the 'test soap bar' with which they washed the volar surface of the right arm for 15 seconds, after which the soap bar was placed aside and they continued lathering for further 45 seconds. The forearm was finally rinsed under warm running tap water and then patted dry by the study investigator using tissue. The procedure was repeated for the left arm of the same subject using the other test soap bar. After treatment subjects were allowed to return to their daily routine and asked to return six hours later. Subjects were asked to avoid washing/wetting their forearms for the remainder of the day.

Upon their return each subject was seated while three labelled inoculated petri dished were placed in contact with each volar surface for 30 minutes; the plates were kept in place using surgical bandaging. After 30 minutes contact, the dishes were removed and the subject's arms were disinfected with an ethanol rinse/wipe followed by washing with antibacterial soap. Control petri dishes (also surface inoculated with S. aureus) were not placed in contact with any subject's forearm. The test and control dishes were incubated for 24–48 hours and then the numbers of developed colonies were counted.

Statistical Analyses—Wilcoxon Signed-rank Test

The average colony count of the 3 agar plates was calculated for each arm washed (6 hours) previously with the appropriate test soaps. The differences in average colony count between arms due to the soaps used were determined and ranked in order of magnitude, irrespective of the sign (i.e. given a rank order). Panellists showing no differences in scores between the two soaps were excluded from the analysis.

The sign of the ranking was then taken into consideration. The rank order scores were totalled as two groups (− or +) and the lower score was compared with statistical tables to check for significance.

Results

Set A

| Base + 0.18% triclosan vs Base + 0.23% triclosan | |
| --- | --- |
| When tested against S. aureus: | significant difference at 99% |
| When tested against E. coli: | significant difference at 90% |

The results for both S. aureus and E. coli demonstrate that the agar patch test, 6 hours after a single wash, is sensitive enough to discriminate between the two levels of triclosan (0.18% & 0.23%). The statistical analyses confirmed that the soap bar with the higher level of triclosan (0.23%) was more effective at inhibiting the growth of both the S. aureus and E. coli on agar petri dishes after a single wash 6 hours previously.

Set B

| Base + 0.23% triclosan + TS 118L vs Base + 0.18% triclosan + BioPink | |
| --- | --- |
| When tested against S. aureus: | no significant difference |
| When tested against E. coli: | no significant difference |

In this comparison (set B) no significant difference was found, for either S. aureus or E. coli, between soap base containing 0.23% triclosan and perfumed with the TS 118L and the soap base containing the reduced level of triclosan (0.18%) and perfumed with BioPink. In terms of actual colony counts this meant that the numbers of bacteria that were inhibited by either soap bars were very similar.

Set C

| Base + 0.18% triclosan + TS 118L vs Base + 0.18% triclosan + BioPink | |
|---|---|
| When tested against *S. aureus:* | significant at 95% |
| When tested against *E. coli:* | significant at 90% |

In this test (set C), the only variable in the soap was the perfume (the level of triclosan was the same, 0.18%). The statistical analysis showed that when the forearms were washed with the soaps, the bar perfumed with BioPink inhibited the growth of *S. aureus* and *E. coli* significantly (at 95% and 90% levels, respectively), demonstrating that the BioPink perfume was more effective than the TS 118L perfume.

Set D

| Base only vs Base + 0.18% triclosan + BioPink | |
|---|---|
| When tested against *S. aureus:* | significant difference at 99% |
| When tested against *E. coli:* | significant difference at 95% |

This set was tested to ensure that the bar with triclosan (0.18%) and perfumed with BioPink was more effective at inhibiting bacteria than the soap bar containing neither of these ingredients. The statistical analysis demonstrated that for both species (*S. aureus* and *E. coli*) the bar containing the triclosan and BioPink perfume was more effective than the bar without either of these ingredients.

Conclusions

The statistical analysis from set A showed that the agar patch test after a single wash, 6 hours previously, was sensitive enough to discriminate between a difference of 0.05% triclosan in the rCN soap base. This was observed through the presence of fewer bacterial colonies on agar plates that had been in contact with arms washed with the higher level of triclosan. Statistical analysis of data (colony counts) from arms washed with set B soaps showed that there was no statistical difference between the bar containing the higher level of triclosan (0.23%) and perfumed with TS 118L and the bar with a reduced level of triclosan (0.18%) and perfumed with BioPink—i.e. they both effectively inhibited bacterial growth to the same degree. This clearly demonstrated that the bar with reduced triclosan (0.18%) and perfumed with BioPink matched the antibacterial efficacy of the conventional formulation of 0.23% triclosan+TS 118L.

The agar patch test was carried out on set C soap bars to confirm that the bar perfumed with BioPink was more effective at inhibiting bacterial growth for both the Gram positive species (*S. aureus*) and the Gram negative species (*E. coli*) than the bar perfumed with TS 118L but containing the same level of triclosan (0.18%). The final two Agar Patch tests against *S. aureus* and *E. coli* reinforced that the soap bar containing triclosan (0.18%) and perfumed with BioPink was more effective at bacterial inhibition of both species than the unperfumed bar containing no active.

What is claimed is:

1. A perfumed product comprising at least one antibacterial agent selected from the group consisting of triclosan, 2,2'-methylene bis (3,4,6-trichlorophenol), 2,4,4'-trichlorocarbanilide, 3,4,4'-trichlorocarbanilide, 2,5,4'-tribromosalicylanilide, 3-trifluoromethyl-4,4'-dichlorocarbanilide, hexachlorophene, dichlorophenol, trichlorosalycilanilide, tribromosalycilanilide (TBS), and tetrachlorosalycilanilide (TCSA); and a mixture of perfume materials having antibacterial properties comprising dodecahydro-3a,6,6,9a-tetramethylnaphtho[2,1-b]furan, clover leaf, dihydro myrcenol, phenyl propyl alcohol and terpineol alpha.

2. The perfumed product according to claim 1, wherein the antibacterial agent is present in an amount in the range 0.01 to 10% by weight.

3. A perfumed product comprising one of the following mixtures of perfume ingredients containing the following perfume materials in the specified amounts (by weight):

| Ingredient | Mixture 1 | Mixture 2 | Mixture 3 |
|---|---|---|---|
| dodecahydro-3a,6,6,9a-tetramethylnaphtho[2,1-b]furan | 0.50 | 0.40 | 0.50 |
| Citronellol standard | — | 2.70 | 2.70 |
| Clove leaf | 4.50 | 3.20 | 3.60 |
| Dihydro myrcenol | 5.50 | 3.50 | 3.50 |
| Styrally acetate | 3.00 | 2.00 | 2.00 |
| Benzyl alcohol | 10.00 | — | 10.40 |
| Ethyl vanillin | 0.10 | 0.10 | 0.10 |
| Moss oakmoss | — | 0.40 | 0.40 |
| Phenyl propyl alcohol | 2.70 | 2.00 | 2.00 |
| Terpineol alpha | 9.00 | 6.00 | 6.00 |
| Tetrahydro linalol | — | 3.00 | 3.00. |

4. The perfumed product according to claim 1 or 3, wherein the product comprises soap.

5. The perfumed product according to claim 1, wherein the perfume material mixture is present in an amount in the range 0.01 to 90% by weight.

6. In a perfumed composition having antibacterial activity, the improvement comprising a combination of triclosan as antibacterial agent and a perfume mixture comprising dodecahydro-3a,6,6,9a-tetramethylnaphtho[2,1-b]furan, clover leaf, dihydro myrcenol, phenyl propyl alcohol and terpineol alpha, said perfume mixture having antibacterial properties and enabling the use of a reduced amount of the antibacterial agent without reducing the antibacterial efficacy of the composition.

7. The perfumed product according to claim 1 or 6 which also includes 2,4,4'-trichlorocarbanilide or 3,4,4'-trichlorocarbanilide as the as antibacterial agent.

* * * * *